(12) United States Patent
Albertson

(10) Patent No.: US 7,595,497 B2
(45) Date of Patent: Sep. 29, 2009

(54) FUEL CONTAMINANT LIGHT SENSOR

(75) Inventor: William C. Albertson, Clinton Township, MI (US)

(73) Assignee: GM Global Technology Operations, Inc., Detroit, MI (US)

( * ) Notice: Subject to any disclaimer, the term of this patent is extended or adjusted under 35 U.S.C. 154(b) by 242 days.

(21) Appl. No.: 11/690,880

(22) Filed: Mar. 26, 2007

(65) Prior Publication Data

US 2008/0237503 A1 Oct. 2, 2008

(51) Int. Cl.
*G01N 21/00* (2006.01)
*G01N 15/06* (2006.01)
(52) U.S. Cl. .................. 250/573; 250/564; 356/436
(58) Field of Classification Search .......... 250/564, 250/573–577; 356/436–442, 246; 73/293, 73/861
See application file for complete search history.

(56) References Cited

U.S. PATENT DOCUMENTS

| | | | | |
|---|---|---|---|---|
| 3,060,318 | A | * 10/1962 | Ouvrard | 250/573 |
| 4,015,121 | A | * 3/1977 | Gagnon et al. | 250/221 |
| 5,453,197 | A | 9/1995 | Strefling | |
| 2006/0054551 | A1 | 3/2006 | Myers et al. | |

* cited by examiner

*Primary Examiner*—Kevin Pyo
*Assistant Examiner*—Don Williams

(57) ABSTRACT

A fuel contaminant sensor is provided. The fuel containment sensor includes a fluid reservoir having an inlet and an outlet. A light source for projecting a light beam through the fluid reservoir is disposed on the fluid reservoir. A light beam detector for receiving the light beam projected through the fluid reservoir is disposed opposite the light source. A controller is provided for activating the light source and for receiving an output of the light beam detector. An interruption of the light beam inhibits the light beam detector from receiving the light beam.

26 Claims, 2 Drawing Sheets

FUEL CONTAMINANT LIGHT SENSOR

FIELD

The present disclosure relates to contaminant sensing, and more particularly to a fuel contaminant light sensor.

BACKGROUND

The statements in this section merely provide background information related to the present disclosure and may or may not constitute prior art.

Diesel engine fuel systems are sensitive to the presence of water and other contaminants in the diesel fuel. Since water does not provide the lubricity required for the tight fitting components of the diesel engine fuel system, the presence of water in the diesel fuel can cause wear on the components. In addition, water often contains biological and chemical corrosives that can cause degradation of the diesel fuel system components. As such, many diesel fuel systems use fuel-water separators to remove water and other contaminants from the diesel fuel.

Fuel-water separators are typically coupled to a fuel line between the source of the diesel fuel and the engine. Fuel-water separators typically include a reservoir that collects the water and other contaminants after they have been separated from the diesel fuel. While these fuel-water separators work well for their intended purpose, the reservoir needs to be interrogated to determine if the volume of captured water is such that it needs to be drained and serviced. One form of interrogation known in the art is periodic visual inspection through the optically clear reservoir of the fuel-water separator.

In recent years, electrically based sensors using electrodes have been added to the fuel-water separators to trigger a warning signal indicating that the reservoir needs to be drained. An electric potential is impressed upon these electrodes which is not conducted through the electrically non-conductive diesel fuel. However, when electrically conductive water is present, the electric potential is conducted through the water, thereby indicating the reservoir needs draining. While these electric sensors have worked well in the past, the electrodes of the electric sensors are possibly subject to some of the corrosive elements within the diesel and fuel contaminants. Therefore, there is room in the art for an improved non-conductive water sensing system.

SUMMARY

In one aspect of the present invention a fuel contaminant light sensor is provided.

In another aspect of the present invention the light sensor includes a fluid reservoir having an inlet and an outlet, a light source for projecting a light beam through the fluid reservoir, a light beam detector for receiving the light beam projected through the fluid reservoir, and a controller for activating the light source and receiving an output of the light beam detector. An interruption of the light beam inhibits the light beam detector from receiving the light beam.

In still another aspect of the present invention the interruption is due to a change of an index of refraction of a fluid between the light source and the receiver.

In still another aspect of the present invention the interruption is due to a change of index of refraction due to the introduction of a second fluid within the reservoir between the light source and the receiver.

In still another aspect of the present invention the second fluid has an index of refraction different than an index of refraction of the first fluid.

In still another aspect of the present invention the first fluid and the second fluid define an interface between the first fluid and the second fluid.

In still another aspect of the present invention the light beam is refracted when the interface is disposed above the receiver and below the light source.

In still another aspect of the present invention the interruption is due to droplets of a second fluid passing across the path of the light beam.

In still another aspect of the present invention the light source is positioned near a top of the reservoir and the detector is positioned near a bottom of the reservoir.

In still another aspect of the present invention the light source pulses the light beam.

In still another aspect of the present invention the light source continuously emits the light beam.

In still another aspect of the present invention the light source is a laser.

In still another aspect of the present invention the light source is a light emitting diode.

In a second aspect of the present invention a device for detecting a change in the contents of a fuel-water separator is provided.

In another aspect of the present invention the device includes a fluid reservoir for containing a fluid, an emitter/detector coupled to the reservoir for emitting a light beam through the fluid and for detecting the light beam, a controller in electronic communication with the emitter/detector. The controller is operable to activate the emitter/detector to emit the light beam and operable to determine whether the light beam has been detected. A reflector is coupled to the reservoir. The reflector is in alignment with the emitter/detector such that the light beam emitted from the emitter is reflected by the reflector back to the emitter/detector. An interruption of the light beam between the emitter/detector and the reflector prevents the emitter/detector from detecting the light beam.

In still another aspect of the present invention, the interruption is due to a change of index of refraction due to the introduction of a second fluid within the reservoir between the emitter/detector and the reflector.

In still another aspect of the present invention the second fluid has an index of refraction different than an index of refraction of the first fluid.

In still another aspect of the present invention the first fluid and the second fluid define an interface therebetween.

In still another aspect of the present invention the interface refracts the light when the interface is disposed above the reflector and below the emitter/detector.

In still another aspect of the present invention the interruption is due to a change of index of refraction in the fluid.

In still another aspect of the present invention the interruption is due to droplets of a second fluid passing across the path of the light beam.

In still another aspect of the present invention the emitter/detector pulses the light beam.

In still another aspect of the present invention the emitter/detector continuously emits the light beam.

In still another aspect of the present invention the emitter/detector includes a laser.

In still another aspect of the present invention the emitter/detector includes a light emitting diode.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1A:
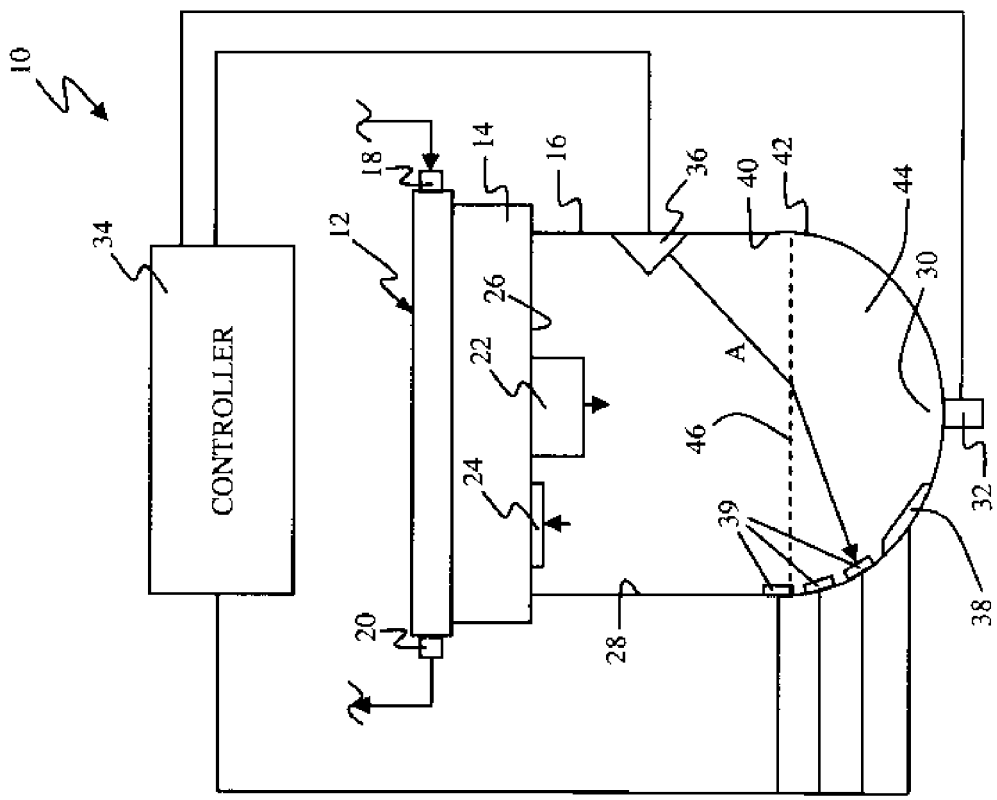
FIG. 1A is a schematic view of a fuel-water separator having a first embodiment of a water sensing system according to the principles of the present invention.

FIG. 1A illustrates a sensing system 10 according to the principles of the present invention. The sensing system 10 is illustrated in operation with an exemplary fuel-water separator 12. However, it should be appreciated that the sensing system 10 may be employed with any structure having a reservoir for containing a substance, such as a fuel tank or storage container. The fuel-water separator 12 is typically located between a fuel supply (not shown) and an engine (not shown) of a motor vehicle (not shown). The fuel-water separator 12 is operable to separate water and other contaminates from fuel, as will be described in further detail below. The fuel-water separator 12 generally includes a ported housing 14 and a cup-shaped reservoir 16. The housing 14 includes an inlet port 18 for receiving a fuel from the fuel supply (not shown) and an outlet port 20 for discharging the fuel once water and contaminates have been removed. The housing 14 further includes a fuel discharge port 22 and a fuel return port 24 located on a bottom surface 26 of the housing 14. The reservoir 16 is sealingly secured to the bottom surface 26 such that the fuel discharge port 22 and fuel return port 24 are located within a cavity 28 defined by the reservoir 16 and the housing 14.

During operation of the fuel-water separator 12, fuel from the fuel supply (not shown) enters the housing 14 via the inlet port 18. The fuel passes through a flow passage (not shown) within the housing 14 and is discharged into the reservoir 16 via the fuel discharge port 22, as indicated by the downward arrow. Water and contaminants, which are heavier than the fuel, settle to a quiet zone 30 located at the bottom of the reservoir 16. The fuel then returns to the housing 14 via the fuel return port 24, as indicated by the upward arrow. The fuel may then be further filtered within the housing 14 before being discharged from the fuel-water separator 12 via the outlet port 20. To remove water or contaminants from the quiet zone 30, the fuel-water separator 12 includes a drain valve 32 located at the bottom of the reservoir 16. The drain valve 32 communicates between the reservoir and the surrounding environment. Opening the drain valve 32 allows the contents of the reservoir 16 to be discharged therefrom.

The sensing system 10 includes a controller 34 in electronic communication with an emitter 36, or light source, and a receiver 38. In an alternate embodiment, the controller 34 is in electronic communication with the drain valve 32 in order to automatically open or close the drain valve 32. The controller 34 is an electronic device having a preprogrammed digital computer or processor, control logic, memory used to store data, and at least one I/O section. The control logic includes a plurality of logic routines for monitoring, manipulating, and generating data. The controller 34 may be part of the control for a motor vehicle or a separate module.

The emitter 36 is secured to the reservoir 16, as will be described in further detail below. The emitter 36 is operable to emit a light beam therefrom. The light beam is indicated by the arrow "A" in FIG. 1A and may be coherent light or any other form of light. The emitter 36 may be any kind of light source, such as, for example, a laser or light emitting diode. The emitter 36 may emit the light beam continuously or it may pulse the light beam at predetermined or random intervals for selected time periods. The receiver 38 is also secured to the reservoir 16 and is located generally opposite the emitter 36. The receiver 38 is operable to detect the light beam emitted from the emitter 36. In the preferred embodiment, the emitter 36 and receiver 38 are protected by a layer or coating of non-corrosive materials, such as, for example, glass.

In the particular example provided, the emitter 36 and the receiver 38 are coupled to an inner surface 40 of the reservoir 16. Alternatively, the emitter 36 and the receiver 38 may be coupled to an outer surface 42 of the reservoir 16 so long as the emitter 36 is able to emit the light beam through the reservoir 16. This may be accomplished by employing a transparent reservoir 16 made from a material having a known index of refraction or by providing ports through the reservoir 16 for the emitter 36 and receiver 38 to extend therethrough.

The emitter 36 and receiver 38 are positioned within the reservoir 16 such that the light beam is directed from the emitter 36 towards the receiver 38. So long as any substance, such as fuel or air, located within the cavity 28 has a constant index of refraction, the light beam emitted from the emitter 36 will be detected by the receiver 38.

The controller 34 communicates with the emitter 36 to activate the light beam and communicates with the receiver 38 to determine whether the light beam has been detected by the receiver 38. If the light beam is directed from the emitter 36 to the receiver 38 without interruption, then the receiver 38 will communicate with the controller 34 that the receiver 38 is detecting the coherent light beam. This detection of the light beam is indicative that there is no interruption of the light beam, indicative that there is no change of index of refraction of the fuel within the cavity 28 of the fuel-water separator 12 and indicative that the reservoir 16 does not need to be drained of water or contaminants.

in an alternate embodiment the sensing system 10 includes a plurality of receivers 39 located on the reservoir 16 opposite the emitter 36. Alternatively, the receivers 38 and 39 may form one single strip sensor that extends along the reservoir 16. The plurality of receivers 39 are in electronic communication with the controller 34. Like the receiver 38, the additional plurality of receivers 39 are operable to communicate with the controller 34 that the plurality of receivers 39 are detecting the light beam. As will be described in greater detail below, the plurality of receivers 39 will only detect the light beam when the light beam has been redirected within the reservoir 16.

Figure 1B:
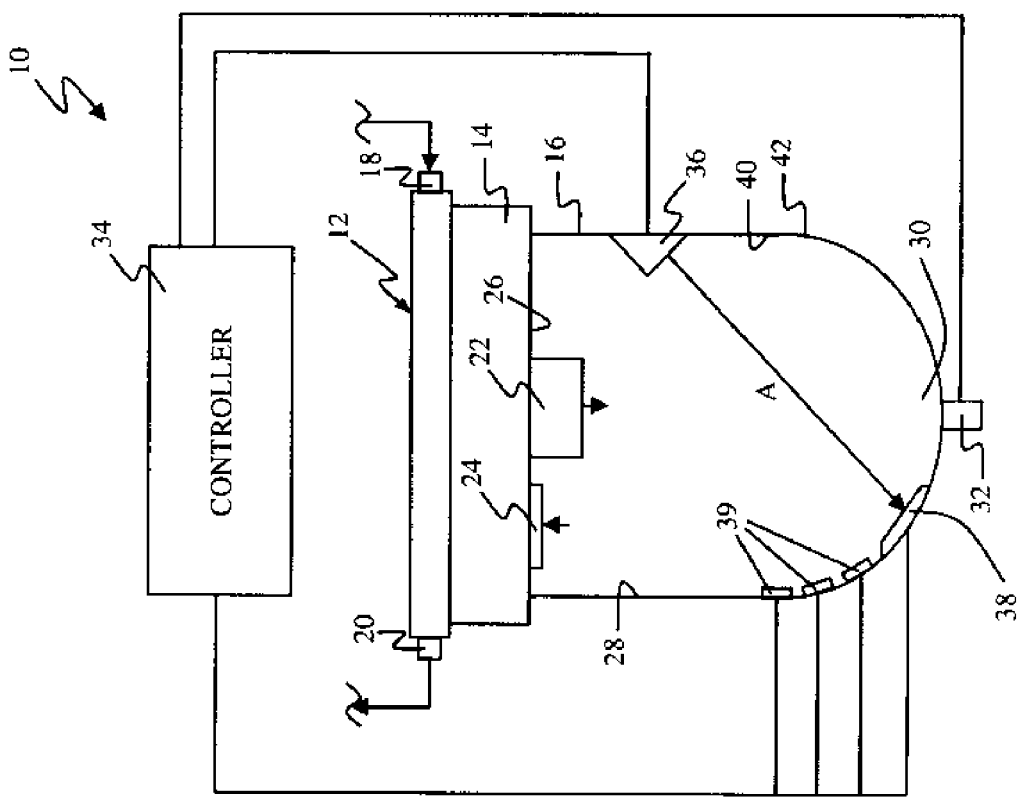
FIG. 1B is a schematic view of a fuel-water separator having the first embodiment of the water sensing system of the present invention with water present in the fuel-water separator.

Turning now to FIG. 1B, if water is contained within the fuel as it enters the fuel-water separator 12, this water will settle to the quiet zone 30 of the reservoir 16 where the water will accumulate, as indicated by reference number 44. The water 44 in part defines an interface 46 between the water 44 and any other substance, such as fuel or air, within the cavity 28. While water 44 is illustrated in the particular example provided, it should be appreciated that various other contaminants may separate out of the fuel and behave in the same manner as the water 44.

As the amount of collected water 44 increases, the interface 46 of the water 44 will rise towards the bottom surface 26 of the housing 12. Eventually, the interface 46 of the water 44 will rise above the receiver 38 within the reservoir 16, as is illustrated in FIG. 1B. Once the interface 46 of the water 44 has risen above the receiver 38, the water 44 will be in a direct line with the light beam emitted from the emitter 36. As the light beam passes through the interface 46 of the water 44, the light beam is refracted such that the light beam is no longer directed towards the receiver 38. This refraction of the light beam occurs because the water 44 has an index of refraction different from the index of refraction of the fuel or air located within the cavity 28. For example, the fuel within the cavity 28 has an index of refraction of approximately 1.44 while the water 44 has an index of refraction of approximately 1.33. The position of the receiver 38 with respect to the reservoir 16 determines how much water 44 is allowed to accumulate before the light beam is refracted. In the example illustrated in FIGS. 1A and 1B, the receiver 38 is located near the bottom of the reservoir 16 such that a small amount of water 44 within the reservoir 16 will refract the coherent light beam. Alternatively, the receiver 38 may be positioned on the reservoir 16 closer to the bottom surface 26 of the housing 14 to allow more water 44 to accumulate before the water 44 refracts the light beam. In this sense, knowing the location of the receiver 38 relative to the reservoir 16 allows the sensing system 10 to know how much water has collected in the reservoir 16.

The light beam also may be attenuated if there is a change in the transparency of the substance within the cavity 28. For example, if the fuel suffers from gelling or clouding due to cold weather, the transparency of the fuel will change, and the light beam will be attenuated such that it is not detected by the receiver 38. Additionally, refraction may occur when water droplets falling from the top of the reservoir 16 to the quiet zone 30 momentarily interrupt the coherent light beam. Such momentary interruption of detection by the receiver 38 may be used to indicate early warning accumulation of water 44 within the reservoir 16.

As noted above, the controller 34 communicates with the emitter 36 to activate the light beam and communicates with the receiver 38 to determine whether the light beam has been detected by the receiver 38. If the presence of the water 44 within the reservoir 16 refracts the light beam, the receiver 38 will communicate with the controller 34 that the receiver 38 is not detecting the light beam. This non-detection of the light beam is indicative of a problem within the fuel-water separator 12. This problem may be that the water 44 within the reservoir 16 should be drained by opening the drain valve 32 or that the fuel is gelling or clouding due to cold weather. Once a problem has been detected, the controller 34 may take various initiatives to alert an operator of the motor vehicle of the problem or to take action to solve the problem. For example, the controller 34 may activate a water warning signal (either digital or analog), send an electronic signal to the motor vehicle control to activate a engine warning signal, automatically open the drain valve 32 using an electronically controlled actuator, or automatically activate a heating element to warm the fuel.

In the embodiment where the sensing system 10 includes the plurality of receivers 39, refraction or attenuation of the light beam can direct the light beam towards one of the plurality of receivers 39. The plurality of receivers 39 then detects the light beam and communicates the detection to the controller 34. Control logic within the controller 34 can use the detection of the light beam from a specific one of the plurality of receivers 39 to determine various conditions within the reservoir 16. For example, the controller 34 may include a look-up table of known indices of refraction for known substances that are often additives of Diesel fuel such as kerosene or biodiesel fuel. As one of the plurality of receivers 39 detects the light beam, the controller 34 may calculate the index of refraction of the substance within the reservoir 16 based on which receiver 39 has detected the light, and use this calculated index of retraction to look up which substance has a matching index of refraction. In this way, the sensing system 10 can determine not only that there has been an interruption of the light beam, but it can also determine what kind of substance is located within the reservoir 16. This may include what kind of fuel is being employed (such as what percentage of biodiesel fuel, kerosene, etc.) or what kind of contaminants are in the reservoir 16 (such as water, sea water, etc.). The use of the plurality of sensors 39 may also be used to determine the water level or contamination level within the reservoir 16 based on the degree of the calculated index of refraction. The controller 34 is operable to track the change in the index of refraction of the fuel within the reservoir 16 over a period of time. The controller 34 may then communicate the determined composition of the fuel to an engine controller (not shown) which can then use the information to adjust combustion parameters.

Figure 2A:
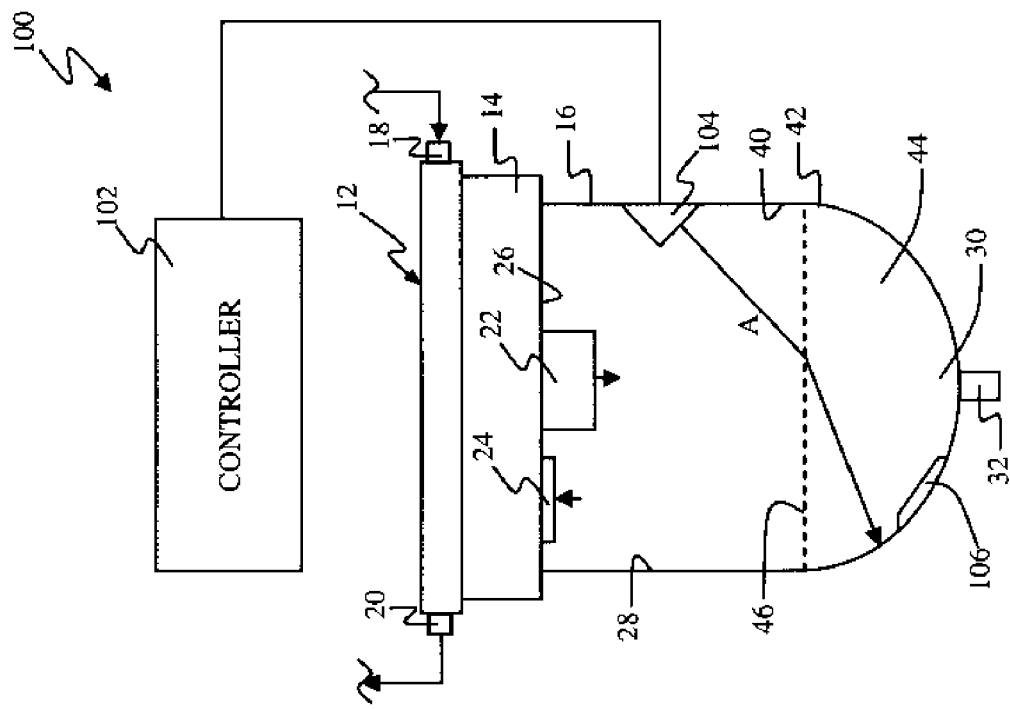
FIG. 2A is a schematic view of a fuel-water separator having a second embodiment of the water sensing system according to the principles of the present invention.

With reference to FIG. 2, a second sensing system 100 is illustrated with the exemplary fuel-water separator 12. The second sensing system 100 includes a controller 102 in electronic communication with an integrated light emitter/detector 104. A reflector 106 is positioned opposite the integrated light emitter/detector 104. The controller 102 is an electronic device having a preprogrammed digital computer or processor, control logic, memory used to store data, and at least one I/O section. The control logic includes a plurality of logic routines for monitoring, manipulating, and generating data. The controller 102 may be part of the control for a motor vehicle or a separate module.

The integrated light emitter/detector 104 is coupled to the reservoir 16, as will be described in further detail below. The integrated light emitter/detector 104 is operable to emit a light beam therefrom and is operable to detect a returning light beam. The light beam is indicated by the arrow "A" in FIG. 2A. The integrated light emitter/detector 104 may be any kind of light source and light detector known in the art. The integrated light emitter/detector 104 may emit the light beam continuously or the integrated light emitter/detector 104 may pulse the light beam at predetermined or random intervals. The reflector 106 is also coupled to the reservoir 16 and is located generally opposite the emitter 36. The reflector 106 has a surface 108 operable to reflect the light beam back towards the integrated light emitter/detector 104. In the preferred embodiment, the integrated light emitter/detector 104 and the reflector 106 are protected by a coating or layer of a non-corrosive material, such as, for example, glass.

In the particular example provided, the integrated light emitter/detector 104 and reflector 106 are coupled to an inner surface 40 of the reservoir 16. Alternatively, the integrated light emitter/detector 104 and the reflector 106 may be coupled to an outer surface 42 of the reservoir 16 so long as the integrated light emitter/detector 104 is able to emit the light beam through the reservoir 16. This may be accomplished by employing a transparent reservoir 16 made from a material having a known index of retraction or by providing ports through the reservoir 16 for the integrated light emitter/detector 104 and the reflector 106 to extend therethrough.

The integrated light emitter/detector 104 and the reflector 106 are positioned within the reservoir 16 such that the light beam is directed from the integrated light emitter/detector 104 towards the reflector 106 which in turn reflects the light beam back towards the integrated light emitter/detector 104. So long as any substance, such as fuel or air, located within the cavity 28 has a constant index of refraction, the light beam emitted from the integrated light emitter/detector 104 will be reflected by the reflector 106 and in turn detected by the integrated light emitter/detector 104.

The controller 102 communicates with the integrated light emitter/detector 104 to activate the light beam and to determine whether the light beam has been in turn detected by the integrated light emitter/detector 104. If the light beam is emitted and detected by the integrated light emitter/detector 104, then the integrated light emitter/detector 104 will communicate with the controller 102 that the integrated light emitter/detector 104 is detecting the light beam. This detection of the light beam is indicative that there is no interruption of the light beam, indicative that there is no change of index of refraction of the fuel within the cavity 28 of the fuel-water separator 12 and indicative that the reservoir 16 does not need to be drained of water or contaminants.

Figure 2B:
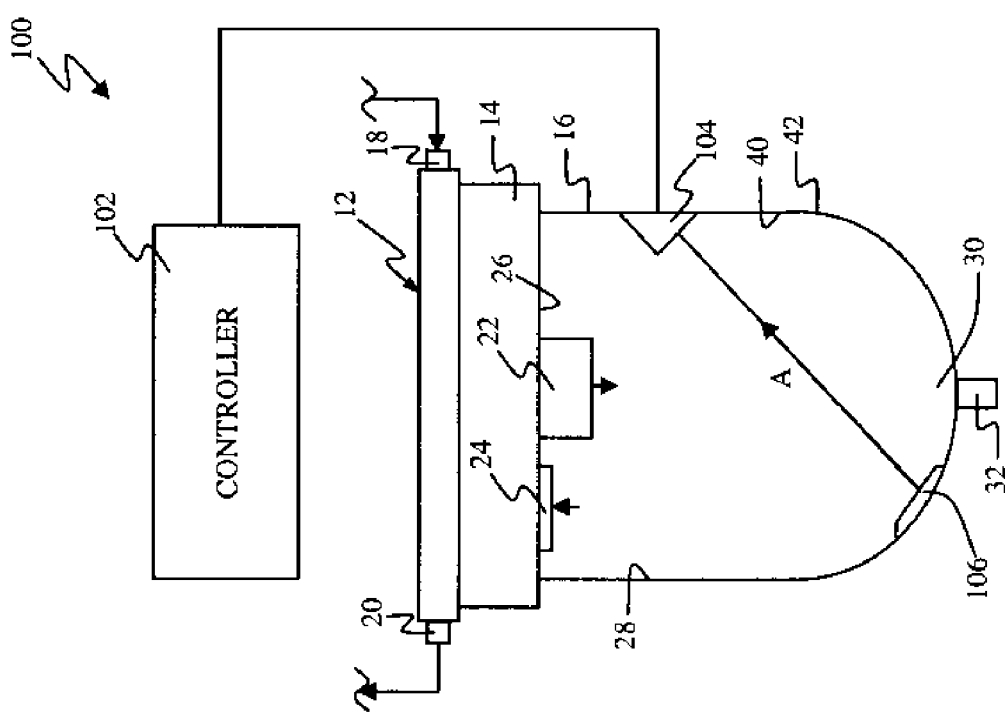
FIG. 2B is a schematic view of a fuel-water separator having the second embodiment of the water sensing system of the present invention with water present in the fuel-water separator.

Turning now to FIG. 2B, water 44 located within the reservoir 16 at a level above the reflector 106 has an effect similar to that described in FIG. 1A. Specifically, as the amount of water 44 that is collected increases, the interface 46 of the water 44 will rise towards the bottom surface 26 of the housing 12. Eventually, the interface 46 of the water 44 will rise above the reflector 106 within the reservoir 16. Once the interface 46 of the water 44 has risen above the reflector 106, the water 44 will be in direct line with the light beam emitted from the integrated light emitter/detector 104. As the light beam passes across the interface 46 of the water 44, the light beam is refracted such that the light beam is no longer directed towards the receiver 38. This refraction of the light beam occurs because the water 44 has an index of refraction different from the index of refraction of the fuel or air located within the cavity 28. The position of the reflector 106 with respect to the reservoir 16 determines how much water 44 is allowed to accumulate before the light beam is refracted.

The light beam also may be attenuated if there is a change in the transparency of the substance within the cavity 28. For example, if the fuel suffers from gelling or clouding due to cold weather, the transparency of the fuel will change, and the light beam will be attenuated such that it is not detected by the integrated light emitter/detector 104.

As noted above, the controller 102 communicates with the integrated light emitter/detector 104 to activate the light beam and to determine whether the light beam has been detected. If the presence of the water 44 within the reservoir 16 refracts the light beam, the integrated light emitter/detector 104 will communicate with the controller 102 that the integrated light emitter/detector 104 is not detecting the light beam. This non-detection of the light beam is indicative of a problem within the fuel-water separator 12. This problem may be that the water 44 within the reservoir 16 should be drained by opening the drain valve 32 or that the fuel is gelling or clouding due to cold weather. Once a problem has been detected, the controller 102 may take various initiatives to alert an operator of the motor vehicle of the problem or to take action to solve the problem. For example, the controller 102 may activate a water warning signal (either digital or analog), send an electronic signal to the motor vehicle control to activate a engine warning signal, automatically open the drain valve 32 using an electronically controller actuator, or automatically activate a heating element to heat the fuel.

The description of the invention is merely exemplary in nature and variations that do not depart from the gist of the invention are intended to be within the scope of the invention. Such variations are not to be regarded as a departure from the spirit and scope of the invention.

What is claimed is:

1. A fuel contaminant sensor comprising:
   a fluid reservoir for containing a first fluid and a second fluid, the fluid reservoir having an inlet and an outlet;
   a light source for projecting a light beam through the fluid reservoir;
   a light beam detector for receiving the light beam projected through the fluid reservoir; and
   a controller for activating the light source and receiving an output of the light beam detector;
   wherein the first fluid and the second fluid define an interface between the first fluid and the second fluid, wherein the interface is disposed between the light source and the light beam detector, and the second fluid has an index of refraction different than an index of refraction of the first fluid; and
   whereby an interruption of the light beam due to a change of index of refraction between the first fluid and the second fluid at the interface inhibits the light beam detector from receiving the light beam.

2. The fuel contaminant sensor of claim 1 wherein the light beam is refracted when the interface is disposed above the receiver and below the light source.

3. The fuel contaminant sensor of claim 1 wherein the interruption is due to droplets of the second fluid passing across the path of the light beam.

4. The fuel contaminant sensor of claim 1 wherein the light source is positioned near a top of the reservoir and the detector is positioned near a bottom of the reservoir.

5. The fuel contaminant sensor of claim 1 wherein the light source pulses the light beam.

6. The fuel contaminant sensor of claim 1 wherein the light source continuously emits the light beam.

7. The fuel contaminant sensor of claim 1 wherein the light source is a laser.

8. The fuel contaminant sensor of claim 1 wherein the light source is a light emitting diode.

9. The fuel contaminant sensor of claim 1 comprising a plurality of light beam detectors located within the fluid reservoir.

10. The fuel contaminant sensor of claim 9 wherein the controller includes logic for calculating an index of refraction of the light beam based on which of the plurality of light beam detectors has detected the light beam and control logic for determining the substance within the fluid reservoir based on the calculated index of refraction.

11. The fuel contaminant sensor of claim 10 wherein the controller includes logic to detect the change in the index of refraction of the light beam over a time period.

12. The fuel contaminant sensor of claim 11 wherein the controller includes logic for communicating to an engine controller the composition of the substance within the fluid reservoir over a period of time.

13. The fuel contaminant sensor of claim 9 wherein the controller includes logic for determining the amount of fluid within the fluid reservoir based on which of the plurality of light beam detectors has detected the light beam.

14. The fuel contaminant sensor of claim 1 further comprising a drain valve coupled to the fluid reservoir and controlled by the controller, the drain valve operable to drain the fluid reservoir.

15. The fuel contaminant sensor of claim 14 wherein the drain valve is opened by the controller when the light beam has been interrupted.

16. The device of claim 1 wherein the first fluid is fuel.

17. A device for detecting a change in the contents of a fuel-water separator comprising:
   a fluid reservoir for containing a first fluid and a second fluid;
   an emitter/detector coupled to the reservoir for emitting a light beam through the first fluid and the second fluid and for detecting the light beam,
   a controller in electronic communication with the emitter/detector, the controller operable to activate the emitter/detector to emit the light beam and operable to determine whether the light beam has been detected; and
   a reflector coupled to the reservoir, the reflector in alignment with the emitter/detector such that the light beam emitted from the emitter is reflected by the reflector back to the emitter/detector; and
   wherein the first fluid and the second fluid define an interface between the first fluid and the second fluid, the interface is disposed between the emitter/detector and the reflector, and the second fluid has an index of refraction different than an index of refraction of the first fluid, and
   wherein an interruption of the light beam due to a change of index of refraction between the first fluid and the second fluid at the interface between the emitter/detector and the reflector prevents the emitter/detector from detecting the light beam.

18. The device of claim 17 wherein the interface refracts the light when the interface is disposed above the reflector and below the emitter/detector.

19. The device of claim 17 wherein the interruption is due to droplets of the second fluid passing across the path of the light beam.

20. The device of claim 17 wherein the emitter/detector pulses the light beam.

21. The device of claim 17 wherein the emitter/detector continuously emits the light beam.

22. The device of claim 17 wherein the emitter/detector includes a laser.

23. The device of claim 17 wherein the emitter/detector includes a light emitting diode.

24. The device of claim 17 wherein the controller includes logic to detect the change in the index of refraction of the light beam over a time period.

25. The device of claim 24 wherein the controller includes logic for communicating to an engine controller that the index of refraction of the fluid has changed.

26. The device of claim 17 wherein the first fluid is fuel.

* * * * *